US007950595B2

(12) United States Patent
Feriani et al.

(10) Patent No.: US 7,950,595 B2
(45) Date of Patent: May 31, 2011

(54) WICKING APPARATUS FOR LIQUID DROPLET SPRAY DEVICE

(75) Inventors: Amir Feriani, Auvernier (CH); Joseph Hess, Bevaix (CH)

(73) Assignee: EP Systems SA, Neuchatel (CH)

( * ) Notice: Subject to any disclaimer, the term of this patent is extended or adjusted under 35 U.S.C. 154(b) by 6 days.

(21) Appl. No.: 12/167,973

(22) Filed: Jul. 3, 2008

(65) Prior Publication Data

US 2009/0045266 A1 Feb. 19, 2009

(30) Foreign Application Priority Data

Jul. 3, 2007 (EP) .................................... 07111659

(51) Int. Cl.
*B05B 1/08* (2006.01)

(52) U.S. Cl. ......... 239/102.2; 239/44; 239/45; 239/328; 222/187

(58) Field of Classification Search ........... 239/44–51.5, 239/86, 102.2, 302, 326, 328; 222/187
See application file for complete search history.

(56) References Cited

U.S. PATENT DOCUMENTS

| | | | | |
|---|---|---|---|---|
| 6,354,513 | B1 * | 3/2002 | Basaganas Millan | 239/44 |
| 6,619,560 | B1 | 9/2003 | Chun | |
| 6,896,196 | B2 | 5/2005 | Vieira | |
| 6,938,833 | B2 * | 9/2005 | Chen | 239/44 |
| 7,017,829 | B2 | 3/2006 | Martens, III et al. | |
| 7,309,024 | B2 * | 12/2007 | Hansen et al. | 239/4 |
| 2002/0136542 | A1 | 9/2002 | He et al. | |
| 2004/0262420 | A1 * | 12/2004 | Hansen et al. | 239/44 |

FOREIGN PATENT DOCUMENTS

| | | | |
|---|---|---|---|
| EP | 1 031 446 | A1 | 8/2000 |
| EP | 1 103 479 | A1 | 5/2001 |
| ES | 2137108 | | 12/1999 |
| WO | 2004/056492 | A1 | 7/2004 |
| WO | 2005/097349 | A1 | 10/2005 |
| WO | 2006/114013 | A1 | 11/2006 |
| WO | 2007/062698 | A1 | 6/2007 |

OTHER PUBLICATIONS

Search Report issued in corresponding European application No. EP 07 11 1659, completed Nov. 22, 2007.
E-Mail from Elson Silva, "Respecting Hydrology Science—US Pat. Application 20090045266", downloaded from ECOLAB, Inc., pp. 1-5, Campinas, SP, Brazil, dated Sep. 29, 2010.

* cited by examiner

*Primary Examiner* — Christopher S Kim
(74) *Attorney, Agent, or Firm* — Griffin & Szipl, P.C.

(57) ABSTRACT

This wicking apparatus includes a liquid reservoir, a wick holder, and a wick.

The wick holder has a top part for fitting on the reservoir neck and a bottom part for insertion into the reservoir opening, the top part being plate-formed with a central opening, and with two peripheral projections that are spaced apart and that extend downward from the plate towards the reservoir body, projections for contacting inner and outer walls of the reservoir neck, and a second projection for contacting an outer wall of the reservoir neck, the bottom part having wick supporting arms that extend downwards and have flexible end portions projecting inwardly towards the centre of the reservoir opening. The wick is step-shaped with a larger diameter part, and a smaller diameter part: the interface between them defines a shoulder which is supported and held in place by the flexible end portions of the supporting arms.

8 Claims, 6 Drawing Sheets

WICKING APPARATUS FOR LIQUID DROPLET SPRAY DEVICE

This application claims priority from European Patent Application No. 07111659.4, filed Jul. 3, 2007, the entire disclosure of which is incorporated herein by reference.

FIELD OF THE INVENTION

The present invention relates to the atomization of liquids in a liquid droplet dispensing device, and more specifically to a wicking apparatus for such a device.

BACKGROUND OF THE INVENTION

Such droplet dispensing devices, as those of the present invention, are also sometimes called atomizers, nebulizers and the like. They normally contain a nozzle body on a support part, in particular, a nozzle body of a liquid droplet spray device which dispenses a liquid substance as a liquid droplet spray from the device through the nozzles of the nozzle body. They further consist of an actuator based on a vibrating element which generally causes the liquid to vibrate, to be accelerated and expelled as droplets. They further consist of elements such as liquid space, liquid feed and fluid interface to a reservoir, a reservoir as well as electrical connections between the vibrating element and a corresponding electronic circuitry. Such elements may be contained in the aforementioned support part, in a further support part or they may be contained in a number of support parts. The liquid may be for example an ambient fragrance, a perfume, an insecticide, a liquid pharmaceutical formulation, aqueous based liquids and flammable or combustible liquids.

Such nozzle bodies are sometimes called aperture plates, nozzle arrays, dosing apertures, orifice plates, vibratable membrane members, dosing aperture arrangements, aerosol generators and the like. These terms are hence to be understood as being interchangeable throughout the present document.

Such nozzle bodies and droplet spray devices are well known as such. For example, the document WO2007/062698, in the name of the present Applicant, describes a liquid droplet spray device having a top substrate formed of a main body and of a nozzle body. The nozzle body contains a nozzle array of liquid droplet outlet means allowing a liquid substance contained in the liquid droplet spray device to exit the device, in this case as a spray of droplets. Liquid may be supplied from a replaceable reservoir by way of a wick using capillary flow. Generally, the reservoir is a dispensable refill that needs to be replaced regularly.

The document U.S. Pat. No. 7,017,829 describes a liquid droplet spray device having a wicking apparatus with a wick for use in a replaceable reservoir assembly that contains liquid to be atomized by a vibratory aperture plate configured to dispense the liquid from the reservoir assembly through the orifices of the vibratory plate. In this device, the wick must contact the vibratory plate to allow for capillary flow of liquid from the reservoir to the plate for ejection of the liquid.

Thus, in order to ensure capillary flow, typically, the wick is too long, so that any fabrication tolerance, which might lead to a wick that would be too short, will be overcompensated.

Furthermore, in order to obtain an acceptable draining ratio of the reservoir, the wick should fully contact the inner bottom surface of the reservoir for it to be capable to substantially drain and empty the reservoir. Indeed, if the wick does not reach the plate, no spray can be generated or ejected.

To ensure such contact, again, the wick is typically oversized so as to compensate for manufacturing tolerances.

However, when a wick that is too long than actually designed is inserted into the reservoir, and positioned below the orifice plate, the wick will inevitably be compressed against the plate and against the inner bottom surface of the reservoir. This compression of the wick then leads to unreliable priming and irregular ejection of liquid each time a reservoir is changed.

In fact, by compressing the wick, which is thus forced into contact to the plate, a so-called squeezing effect is obtained which leads to an increased flow rate of liquid when the wick is first inserted into a replacement reservoir. However, after a certain moment in time, as shown by curve a in FIG. 1, the wick and plate assembly will stabilize in the new position and the flow rate will drop from the increased rate to the intended rate.

Clearly, this is highly undesirable for a consumer, as s/he will have to adjust and re-adjust the flow rate each time the reservoir is replaced in order to have a constant flow rate over time.

Document WO 2005/097349 describes a similar liquid droplet spray device with a wicking apparatus. The wick is formed of two different materials with a rigid main section and a compliant top section. The top compliant section is thus compressible and is pressed into contact with the vibratory orifice plate to allow liquid to flow from the reservoir to the plate by capillary action, and may then be expelled.

Thus, again, the wick is compressed against the plate thus resulting in a squeezing effect, albeit more moderate as compared with the previous document mentioned above, so that here too, an unstable flow rate will occur when inserting a new reservoir.

As for the draining ratio, in this device the rigid main section of the wick would also have to be longer than designed to compensate for manufacturing tolerances and to ensure a full contact with the inner bottom surface of the reservoir.

It is also known to use wick holders so as to correctly and/or securely fix a wick in a reservoir. For example, the document U.S. Pat. No. 6,896,196 describes a liquid droplet spray device with a wicking apparatus that has a wick holder 8 for receiving a wick. The holder is positioned onto a reservoir's bottleneck, and holds the wick in place by way of clamping fingers so as to allow for easy insertion of the wick into the reservoir, while at the same time preventing accidental removal of the wick. However, this document is silent about flow rate or draining ratios.

In view of the above, it is an object of the present invention to provide an innovative wicking apparatus for a droplet spray device that overcomes the inconveniences presented by the prior art documents.

SUMMARY OF THE INVENTION

Further, the proposed wicking apparatus can ensure a constant flow rate even after replacing the reservoir as shown by curve b in FIG. 1, while at the same time allowing for a high draining ratio despite existing manufacturing tolerances of wicks.

Thus, the present invention concerns a wicking apparatus as defined in a first embodiment, namely, a wicking apparatus for volatile substances that may be ejected as a spray of droplets by a liquid droplet dispenser device when fitted with the wicking apparatus, wherein the wicking apparatus includes: (a) a volatile substance reservoir (1); (b) a wick holder (2); and (c) a wick (3), wherein the reservoir (1) has a reservoir body (1*a*) for containing the volatile substance, and a reservoir neck (1*b*) extending from the reservoir body and terminating in a reservoir opening (1*c*) into which the wick holder and the wick may be inserted, and the wick holder (2) has a top part (8) for fitting on the reservoir neck (1*b*) and a bottom part (10) for insertion into the reservoir opening (1*c*), wherein the top part (8) is a plate-formed with a central opening (6) for receiving the wick, and is provided with two peripheral projections (8*a*, 8*b*) that are spaced apart and that extend downward from the plate towards the reservoir body (1*a*) when fitted on the reservoir (1) along substantially the entire periphery of the top part (8), wherein there is a first projection (8*a*) of the two projections for contacting an inner wall of the reservoir neck (1*b*), and a second projection (8*b*) of the two projections for contacting an outer wall of the reservoir neck (1*b*), so that the top part sits on the reservoir supported by the reservoir neck (1*b*) and is held in place by the first and second projections (8*a*, 8*b*), and the bottom part (10) is integrally formed with the first projection (8*a*) and has a plurality of wick supporting arms (10*a*) spaced apart along its periphery, wherein the supporting arms (10*a*) extend further downwards away from the top part (8) and have flexible end portions (10*b*) projecting inwardly towards the centre of the reservoir opening (1*c*), and the wick (3) is step-shaped and has a larger diameter part (3*a*) for supplying, by capillary contact, liquid to a liquid receiving section of the liquid droplet spray device when mounted thereto, and a smaller diameter part (3*b*), as compared to the larger diameter part (3*a*), for extending into the reservoir (1) to contact the inner bottom surface thereof when inserted, wherein an interface between the larger diameter part (3*a*) and the smaller diameter part (3*b*) define a shoulder (3*c*) that is supported and held in place by the flexible end portions (10*b*) of the plurality of supporting arms (10*a*).

In accordance with a second embodiment of the present invention, the first embodiment is modified so that the reservoir (1) is a bottle. In accordance with a third embodiment of the present invention, the first embodiment is modified so that the reservoir (1) is a collapsible bag. In accordance with a fourth embodiment of the invention, the first embodiment, the second embodiment and the third embodiment are further modified so that the wick consists of two separate parts, wherein the larger diameter part has a central opening, and the smaller diameter part is slideably fitted into the larger diameter part.

In accordance with a fifth embodiment of the invention, a liquid droplet spray device is provided that includes a nozzle body, a piezo-electric actuator, a fluid chamber located below the nozzle body and a liquid receiving section, and further includes a wicking apparatus according to anyone of the first embodiment, the second embodiment, the third embodiment and the fourth embodiment of the invention, wherein the liquid receiving section is arranged to receive liquid through capillary contact from the wick, and to provide the chamber with the liquid for ejecting the received liquid as a spray of droplets. In accordance with a sixth embodiment of the invention, the fifth embodiment is further modified so that the liquid receiving section is arranged eccentric with respect to the nozzle body. In accordance with a seventh embodiment of the invention, the fifth embodiment is further modified so that the liquid receiving section is arranged centric with respect to the nozzle body. In accordance with an eighth embodiment of the invention, the seventh embodiment is further modified so that the nozzle body is a vibratory plate.

Thanks to the construction of the innovative and inventive wicking apparatus according to the present invention an efficient device fulfilling the objectives identified above may be obtained in a relatively simple and inexpensive manner.

BRIEF DESCRIPTION OF THE DRAWINGS

Other features and advantages of the wicking apparatus according to the present invention will become clear from reading the following description, which is given solely by way of a non-limitative example thereby referring to the attached drawings in which.

DETAILED DESCRIPTION OF THE INVENTION

A preferred embodiment will now be described.

FIG. 2 shows an example of the wicking apparatus according to the present invention. The wicking apparatus comprises a reservoir 1, a wick holder 2 and a wick 3. FIG. 2*a* shows a general view of the wicking apparatus, whereas FIG. 2*b* shows a top view thereof. FIG. 2*c* shows a cross-sectional view along lines A-A of FIG. 2*a*, and FIG. 2*d* shows a detailed view of section B of FIG. 2*c*.

As can be seen in these figures, reservoir 1 has, in this example, a general bottle shape, with a main body 1*a*, and a bottle neck 1*b*. Wick holder 2 is fitted over the bottleneck 1*b*, and rests thus thereon. A wick 3 is fitted into the wick holder and enters the reservoir to complete the device according to the present invention. Wick 3 extends beyond the top surface of wick holder so as to enter into capillary contact with a liquid receiving means of a liquid droplet spray device so as to allow for ejection of the liquid as a spray of droplets. As will be understood from the following description, this contact is purely a capillary contact, thus avoiding any compression of wick 3 and thus avoiding the so-called squeezing effect which deteriorates stable functioning of prior art devices when an empty reservoir is replaced by a new full one.

Figure 5A:
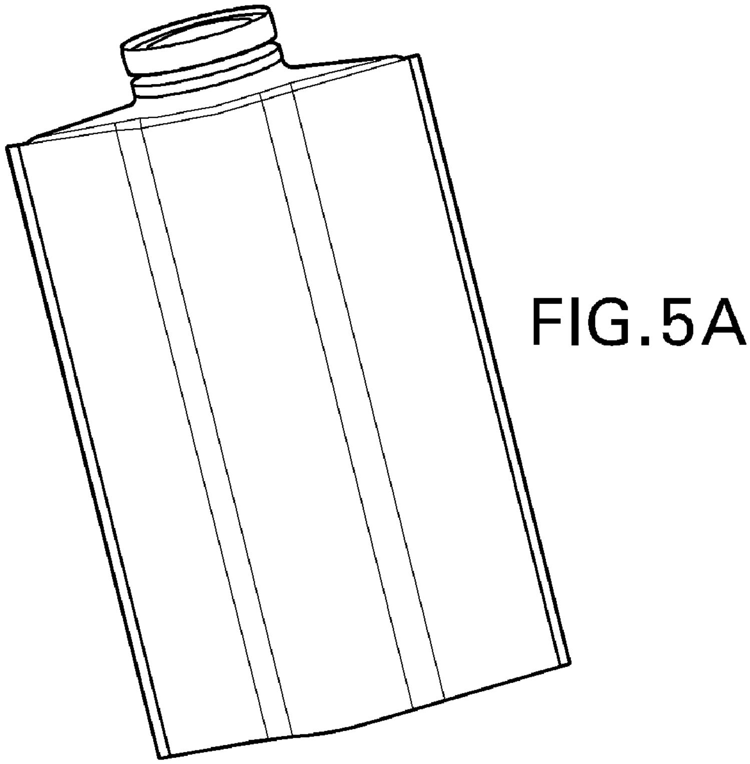
FIG. 5 shows an example of another reservoir for the wicking apparatus according to the present invention.
Figure 5B:
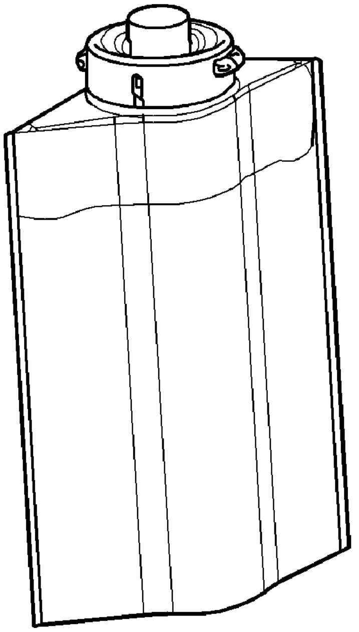

Instead of a bottle shape, reservoir 1 may also be a bag-like reservoir, as shown for example in FIG. 5. Such bag-like reservoir can also be a collapsible bag, as is well known in the art.

Thus, in general, reservoir 1 has a reservoir body 1*a* for containing the volatile substance, and a reservoir neck 1*b* extending from the reservoir body and terminating in a reservoir opening 1*c* (see FIG. 2D) into which a wick holder and a wick may be inserted.

Figure 2A:
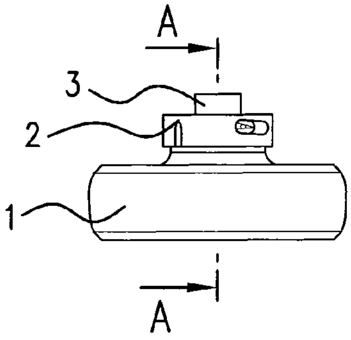
Figure 2D:
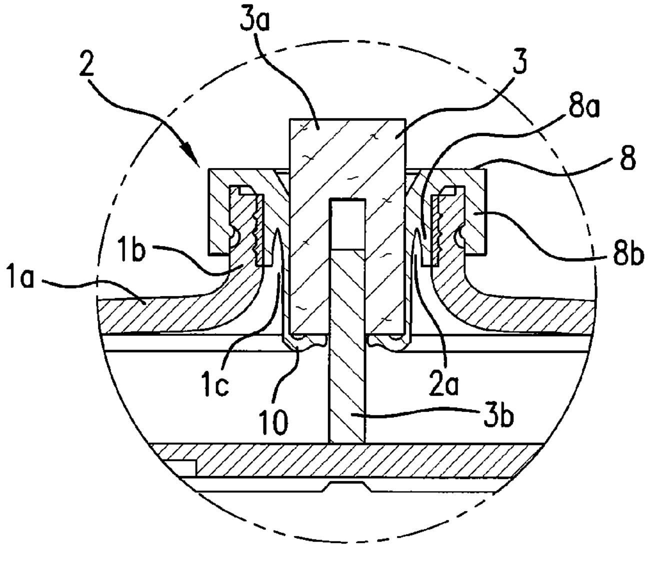
Figure 2C:
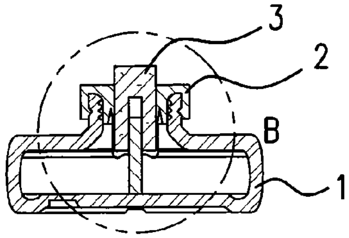
Figure 2B:
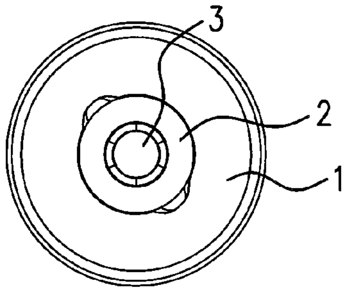

As shown in detail in FIG. 2*d*, wick holder 2 has a top part 8 for fitting over reservoir neck 1*b*, similar to a bottle cap, and a bottom part 10 for insertion into the reservoir opening. Top part 8 is generally flat and plate-formed with a central opening 6 for receiving a wick. At the peripheral edge of top part 8, two projections 8*a*, 8*b* are provided which are spaced apart and which extend downward from the plate towards reservoir body 1*a* when wick holder 2 is fitted onto reservoir 1. In this example, these projections follow substantially the entire periphery of top part 8.

First projection 8*a* is arranged on an inner periphery with respect to the edge of top part 8, and is arranged to contact an inner wall of reservoir neck 1*b*. Second projection 8*b* substantially follows the edge of top part 8 in this example, and is arranged to contact an outer wall of reservoir neck 1*b*. In this way, top part 8 sits on the reservoir supported by reservoir neck 1*b* and held in place by first and second projections 8*a*, 8*b* which pinch together reservoir neck 1*b*.

This arrangement allows for a precise fitting of wick holder 2 on reservoir 1, as the top of reservoir neck constitutes a reference surface.

By using a material for wick holder 2 that can be manufactured with high precision, for example by using a plastic that can be injection-moulded, distances with respect to this reference point can be clearly and accurately defined.

Figure 3:
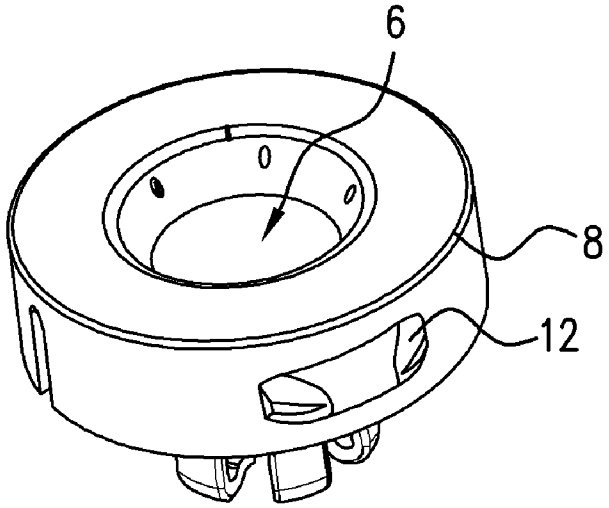
FIG. 3 shows a detailed top-side view of the wick holder shown in FIG. 2.

As shown in FIG. 3, elastic detachment means 12 may be provided on a side surface of second projection 8*b* to allow for secure attachment to reservoir neck 1*b* and for easy removal there from. Such means are well known as such in the art and will not be discussed in more detail here.

Figure 4:
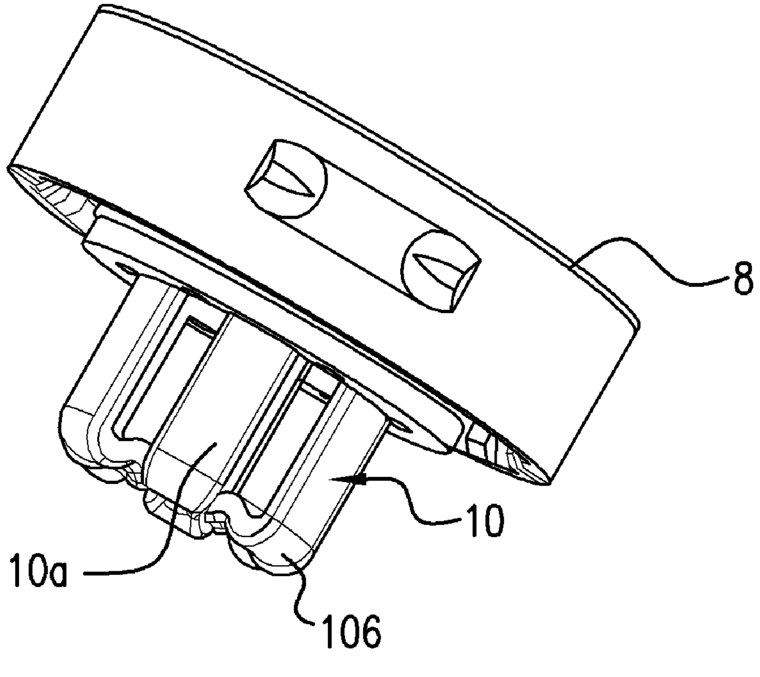
FIG. 4 shows a detailed side view of the wick holder shown in FIG. 2.

FIG. 4 shows a detailed side view of the wick holder shown in FIG. 2. As can be seen in this figure, first projection 8*a* interfaces with integrally formed bottom part 10 that continues further downwards by way of a plurality of wick supporting arms 10*a* spaced apart along the inner edge periphery of first projection 8*a*. These supporting arms 10*a* extend further downwards away from top part 8 and each have a flexible end portion 10*b* projecting inwardly towards the centre of the reservoir opening. These flexible end portions are arranged to allow for a slight vertical displacement by deformation, as will be explained in more detail further on.

Figure 6:
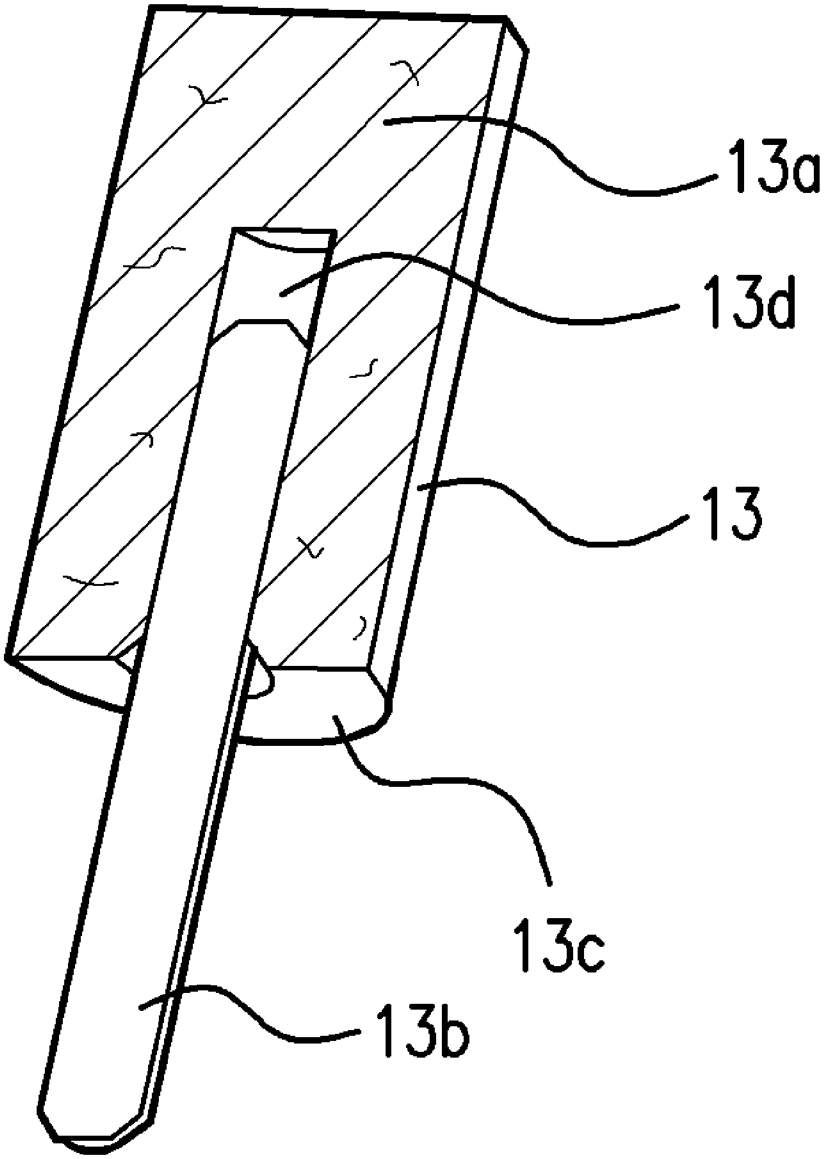
FIG. 6 shows an example of an alternative wick in the wicking apparatus according to the present invention, FIG. 7 sows an example of a liquid droplet spray device to which a wicking apparatus according to the preset invention may be mounted.

As shown in FIG. 2*d* and FIG. 6, wick 3 is step-shaped having a larger diameter upper part 3*a* for supplying by capillary contact liquid to the liquid receiving section of a liquid droplet spray device when mounted thereto, and a smaller diameter lower part 3*b*, as compared to the larger diameter upper part 3*a*, for extending into the reservoir 1 to contact the inner bottom surface thereof when inserted. As can be seen in FIG. 2*d*, the interface between larger diameter upper part 3*a* and smaller diameter lower part 3*b* defines a shoulder 3*c*. When wick 3 is inserted into wick holder 2, this shoulder is supported and held in place by the flexible end portions 10*b* of one or more supporting arms 10*a* of wick holder 8.

Flexible end portions 10*b* can slightly move downwards when a certain weight or pressure is applied thereto. This displacement is larger than the typical fabrication tolerance of a wick. Generally, a wick can be fabricated with a tolerance of its length of around ±0.4 mm. The displacement of the flexible end portion is then chosen, for example, to be 1 mm to allow to fully absorb the manufacturing tolerances. Thus, for example, if a wick is supposed to be 12.7 mm long, in reality it may be between 12.3 and 13.1 mm. A conventional wicking apparatus would then have a wick manufactured with a specified length of at least 13.1 mm, so as to be certain that the wick will be long enough to reach both the bottom inner surface of the reservoir, and to touch the liquid receiving section for inputting the liquid into the spray device.

Thus, typically such a conventional wicking apparatus will use a wick that is too long, and will thus compress the wick into place.

However, according to the present invention, a wick is specified for manufacturing for the correct designed length of 12.7 mm. Such wick will not be compressed, but instead, the flexible end portions 10*b* will move downwards to compensate for any excess length due to manufacturing tolerances.

In fact, the flexible end portions are arranged at a distance such that even a wick with a minimum length of, in this example, 12.7−0.4=12.3 mm will arrive at the correct level above wick holder 2 so as to ensure a capillary contact with the liquid receiving section of a spray device. Any longer wick will cause the flexible end portions to lower so as to absorb the excess length, so that the wick will always arrive at the correct level above wick holder 2 so as to ensure a purely capillary contact with the liquid receiving section of a spray device, free from compression, and thus free from any squeezing effect. If, due to tolerances, the wick is too short, the flexible end portion 10*b* will also compensate such that the wick will always arrive at the correct level above the wick holder.

FIG. 6 shows an example of an alternative wick in the wicking apparatus according to the present invention. In this alternative arrangement, wick 13 also is step-shaped having a larger diameter upper part 13*a* for supplying by capillary contact liquid to the liquid receiving section of a liquid droplet spray device when mounted thereto, and a smaller diameter lower part 13*b*, as compared to the larger diameter upper part 3*a*, for extending into the reservoir 1 to contact the inner bottom surface thereof when inserted. Again, the interface between larger diameter upper part 13*a* and smaller diameter lower part 13*b* defines a shoulder 13*c*. However, these two parts 13*a*, 13*b* are two separate parts, instead of being formed integrally as described above. Larger diameter upper part 13*a* has a central hole 13*d* for receiving smaller diameter lower part 13*b* therein in a slideable manner. As such, the length of wick 13 may vary, and any fabrication tolerances can also be absorbed by the inner relative displacement of smaller diameter lower part 13*b* with respect larger diameter upper part 13*a*.

By combining such a wick 13, with the wick holder 2 described above, any manufacturing tolerance can be compensated for, by the flexible end portions, by the relative displacement of the wick portions, or by a combination of these two.

Figure 7:
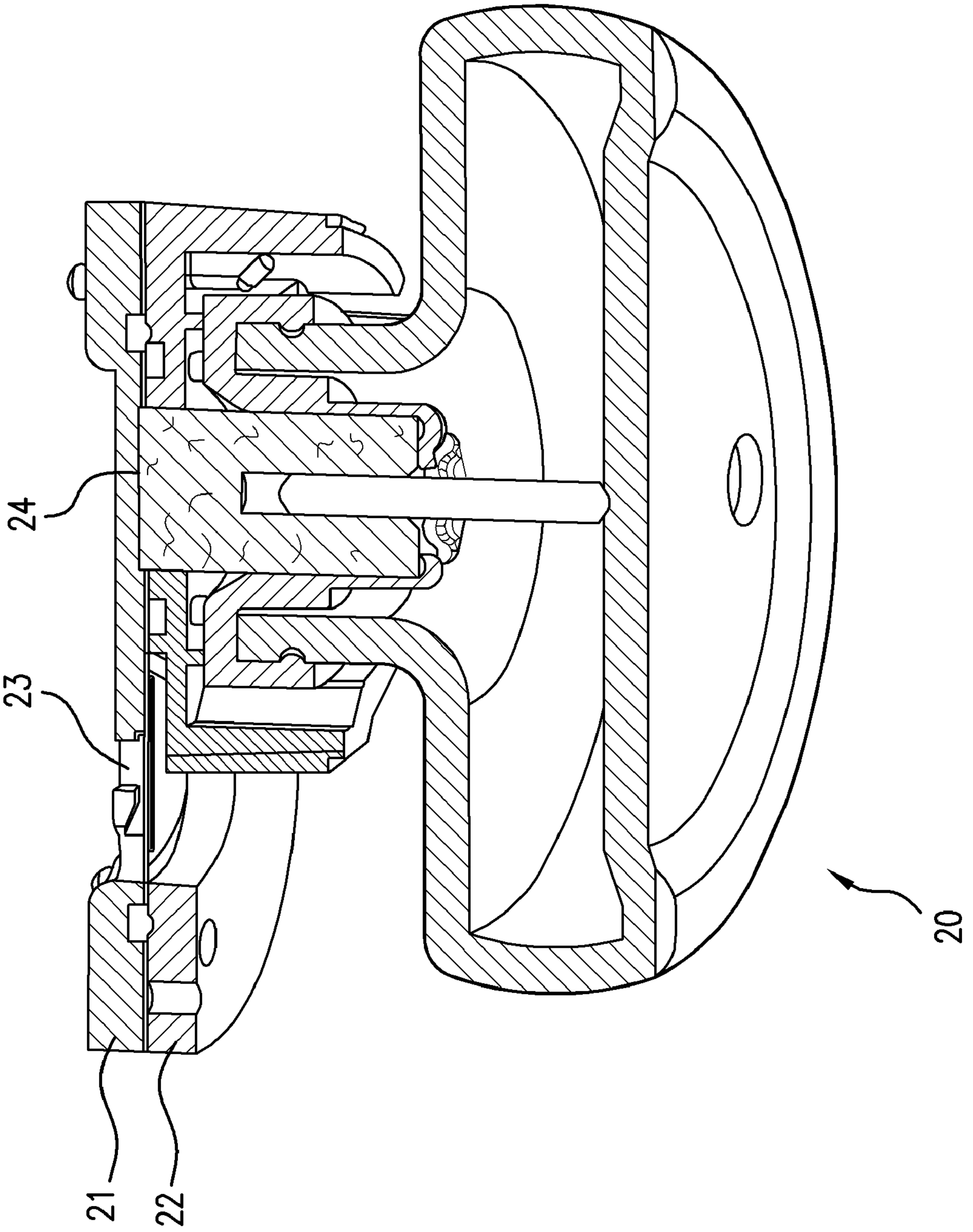

FIG. 7 sows an example of a liquid droplet spray device to which a wicking apparatus according to the preset invention may be mounted. As can be seen, liquid droplet spray device 20 comprises a top package 21, a bottom package 22, liquid outlet means 23, and liquid inlet means 24. More details of this device are described in above-mentioned document WO2007/062698 in the name of the present Applicant Actuating means, such as a piezoelectric vibrating means, not shown, are provided to actuate any liquid present in the liquid outlet means. Liquid outlet means comprises a nozzle array for allowing liquid to exit the spray device once excited. By mounting the wicking apparatus according to the present invention, wick 3, 13 will contact the liquid receiving section of liquid inlet means 24 to allow liquid to enter the spray device by capillary action only. Once the liquid enters the spray device, it is transported to the liquid outlet means 23. Here, the liquid undergoes a vibration, by way of the actuating means, not shown, to excite the liquid so as to expel it through outlet nozzles provided in the outlet means to generate a spray of droplets.

Figure 1:
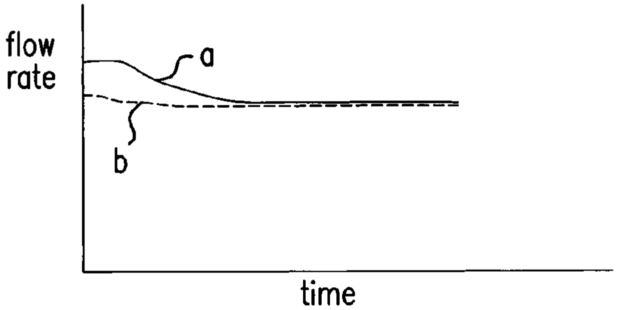
FIG. 1, already mentioned, shows a schematic representation of flow rate versus time in view of a squeezing effect by curve a in conventional devices and by curve b in view of the present invention, FIG. 2 show an example of the wicking apparatus according to the present invention.

Thanks to the present invention, the wick will always be correctly positioned in the liquid receiving means, and will have a capillary contact therewith that is free from compression, despite any manufacturing tolerances of the wick length. This ensures a stable flow rate (curve b in FIG. 1).

Figure 8:
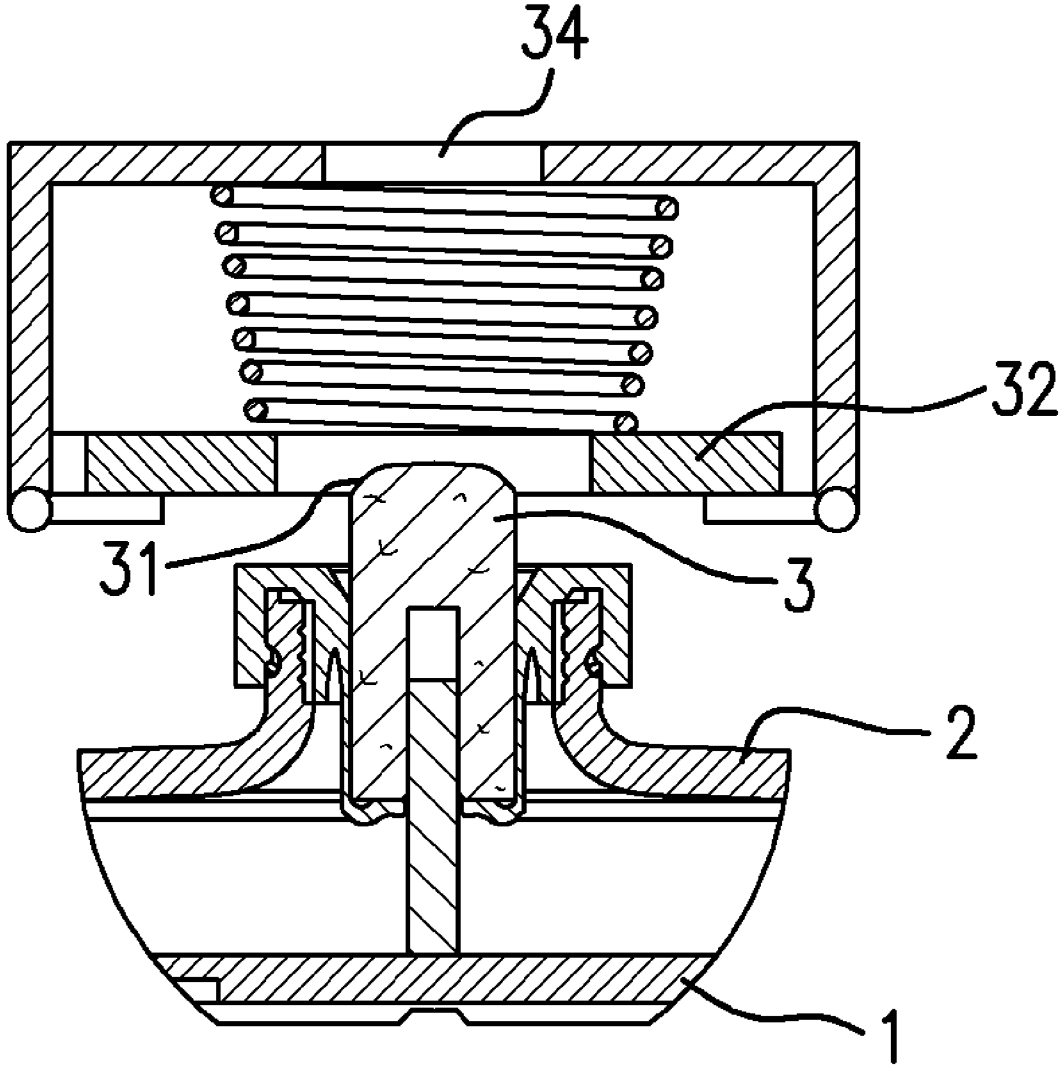
FIG. 8 shows another example of a liquid droplet spray device to which a wicking apparatus according to the preset invention may be mounted.

FIG. 8 shows another example of a liquid droplet spray device to which a wicking apparatus according to the present invention may be mounted. In this spray device, the liquid outlet means take the form of a vibratory dome-shaped nozzle plate, which may be similar to above-mentioned document U.S. Pat. No. 7,017,829. Thus, the liquid inlet means 31 are arranged centrically below the liquid outlet means 34 in that the wick transports the liquid to the bottom of the vibratory plate, which is then excited by suitable vibrating means, for example, circular vibrating element 32 to suck in the liquid into the nozzles of the nozzle plate 31 and to expel the liquid as a spray of droplets through liquid outlet means 34.

Having described now the preferred embodiment of this invention, it will be apparent to one of skill in the art that other embodiments incorporating its concept may be used. It is felt, therefore, that this invention should not be limited to the disclosed embodiment, but rather should be limited only by the scope of the appended claims.

The invention claimed is:

1. A liquid droplet spray device comprising:

(a) a nozzle body;

(b) a piezo-electric actuator;

(c) a fluid chamber located below the nozzle body;

(d) a liquid receiving section; and (e) a wicking apparatus comprising i. a volatile substance reservoir;

ii. a wick holder; and iii. a wick, wherein the reservoir has a reservoir body for containing a volatile substance, and a reservoir neck extending from the reservoir body and terminating in a reservoir opening, wherein the wick holder and the wick are inserted into the reservoir opening; wherein the wick holder has a top part for fitting on the reservoir neck and a bottom part for insertion into the reservoir opening, wherein the top part of the wick holder is in the form of a plate provided with a central opening for receiving the wick, and the plate is provided with two peripheral projections that are spaced apart and that extend downward from the plate towards the reservoir body when fitted on the reservoir along substantially an entire periphery of the top part, wherein the two peripheral projections include a first projection for contacting an inner wall of the reservoir neck, and a second projection for contacting an outer wall of the reservoir neck, so that the top part sits on the reservoir supported by the reservoir neck and is held in place by the first projection and the second projection, wherein the bottom part of the wick holder is integrally formed with the first projection and has a plurality of wick supporting arms spaced apart along a periphery of the bottom part, and the plurality of supporting arms extend further downwards away from the top part and the supporting arms have flexible end portions projecting inwardly towards a center of the reservoir opening; wherein the wick is step-shaped and has a larger diameter part for supplying, by capillary contact, liquid to the liquid receiving section of the liquid droplet spray device when mounted thereto, and a smaller diameter part, as compared to the larger diameter part, for extending into the reservoir to contact an inner bottom surface of the reservoir when inserted in the reservoir, wherein an interface disposed between the larger diameter part and the smaller diameter part defines a shoulder that is supported and held in place by the flexible end portions of the plurality of supporting arms, wherein the liquid receiving section is arranged to receive liquid through capillary contact from the wick, and to provide the fluid chamber with the liquid for ejecting liquid received by the fluid chamber as a spray of droplets exiting through the nozzle body when the liquid is actuated by the piezo-electric actuator.

2. A wicking apparatus according to claim 1, wherein said reservoir is a bottle.

3. A wicking apparatus according to claim 1, wherein said reservoir is a collapsible bag.

4. A wicking apparatus according to claim 1, wherein said wick comprises two separate parts including said larger diameter part and said smaller diameter part, wherein said larger diameter part has a central opening, and said smaller diameter part is slideably fitted into said larger diameter part.

5. A liquid droplet spray device according to claim 1, wherein said liquid receiving section is arranged eccentric with respect to said nozzle body.

6. A liquid droplet spray device according to claim 1, wherein said liquid receiving section is arranged centric with respect to said nozzle body.

7. A liquid droplet spray device according to claim 6, wherein said nozzle body is a vibratory plate.

8. A liquid droplet spray device comprising:

(a) a nozzle body;

(b) a piezo-electric actuator;

(c) a fluid chamber located below the nozzle body;

(d) a liquid receiving section; and (e) a wicking apparatus comprising i. a volatile substance reservoir;

ii. a wick holder; and iii. a wick, wherein the reservoir has a reservoir body for containing a volatile substance, and a reservoir neck extending from the reservoir body and terminating in a reservoir opening, wherein the wick holder and the wick are inserted into the reservoir opening; wherein the wick holder has a top part for fitting on the reservoir neck and a bottom part for insertion into the reservoir opening, wherein the top part of the wick holder is in the form of a plate provided with a central opening for receiving the wick, and the plate is provided with two peripheral projections that are spaced apart and that extend downward from the plate towards the reservoir body when fitted on the reservoir along substantially an entire periphery of the top part, wherein the two peripheral projections include a first projection for contacting an inner wall of the reservoir neck, and a second projection for contacting an outer wall of the reservoir neck, so that the top part sits on the reservoir supported by the reservoir neck and is held in place by the first projection and the second projection, wherein the bottom part of the wick holder is integrally formed with the first projection and has a plurality of wick supporting arms spaced apart along a periphery of the bottom part, and the plurality of supporting arms extend further downwards away from the top part and the supporting arms have flexible end portions projecting inwardly towards a center of the reservoir opening; wherein the wick is step-shaped and has a larger diameter part for supplying, by capillary contact, liquid to the liquid receiving section of the liquid droplet spray device when mounted thereto, and a smaller diameter part, as compared to the larger diameter part, for extending into the reservoir to contact an inner bottom surface of the reservoir when inserted in the reservoir, wherein an interface disposed between the larger diameter part and the smaller diameter part defines a shoulder that is supported and held in place by the flexible end portions of the plurality of supporting arms, and the interface is formed by the larger diameter part that has a central opening, and the smaller diameter part that is slideably fitted into the larger diameter part, wherein the liquid receiving section is arranged to receive liquid through capillary contact from the wick, and to provide the fluid chamber with the liquid for ejecting liquid received by the fluid chamber as a spray of droplets exiting through the nozzle body when the liquid is actuated by the piezo-electric actuator, and wherein the volatile substance reservoir is a collapsible bag.

* * * * *